(12) United States Patent
Warner

(10) Patent No.: US 11,389,419 B1
(45) Date of Patent: Jul. 19, 2022

(54) TREATMENT OF DISORDERS ARISING FROM GENETIC MUTATION

(71) Applicant: Deborah Warner, Houston, TX (US)

(72) Inventor: Deborah Warner, Houston, TX (US)

( * ) Notice: Subject to any disclaimer, the term of this patent is extended or adjusted under 35 U.S.C. 154(b) by 0 days.

(21) Appl. No.: 17/367,606

(22) Filed: Jul. 5, 2021

Related U.S. Application Data

(60) Provisional application No. 63/020,026, filed on May 5, 2020.

(51) Int. Cl.
| | |
|---|---|
| A61K 31/205 | (2006.01) |
| A61K 31/675 | (2006.01) |
| C12Q 1/686 | (2018.01) |
| A61K 31/194 | (2006.01) |

(52) U.S. Cl.
CPC .......... *A61K 31/205* (2013.01); *A61K 31/194* (2013.01); *A61K 31/675* (2013.01); *C12Q 1/686* (2013.01); *C12Q 2600/106* (2013.01)

(58) Field of Classification Search
CPC .. A61K 31/194; A61K 31/205; A61K 31/675; C07C 227/42; C07C 51/43; C07C 229/70; C07C 59/255; C07B 2200/13; C12Q 1/686; C12Q 2600/106
See application file for complete search history.

(56) References Cited

U.S. PATENT DOCUMENTS

2014/0316156 A1* 10/2014 Warner .................... C07C 51/43
560/176

* cited by examiner

*Primary Examiner* — Umamaheswari Ramachandran
(74) *Attorney, Agent, or Firm* — Barry Choobin; Patent 360

(57) ABSTRACT

A method for treatment of disorders arising due to mutation of one or more genes in humans. The method includes the step of orally administering a composition comprising L-carnitine tartrate, pyridoxal-5'-phosphate, and fumaric acid.

6 Claims, No Drawings

TREATMENT OF DISORDERS ARISING FROM GENETIC MUTATION

CROSS-REFERENCE TO RELATED APPLICATIONS

This application claims priority from the U.S. provisional patent application Ser. No. 63/020,026 filed on May 5, 2020, which is incorporated herein by reference in its entirety.

FIELD OF INVENTION

The present invention relates to a method of treatment, and more particularly, the present invention relates to the treatment of disorders arising from specific gene mutations.

BACKGROUND

The field of epigenetics is now key in the research and development of therapies to address pathology in the cells of living organisms. Understanding of various epigenetic mechanisms, like histone modification, DNA methylation, small non-coding RNAs, and gene functionality and regulation has revealed the pathophysiology of various disorders. Research has documented that mutations affecting the DNA Damage Recovery Pathways often lead to mutations in genes as well as to alterations in epigenetic signaling of genes including BRCA1, BRCA2, and MTHFR. Together, these mutations and signaling abnormalities turn off apoptosis signals or turn on senescence signals that leave these cells susceptible to mutation, infection, and toxins. Current genetic scanning technology detects these cellular conditions as abnormal gene sequences, single nucleotide polymorphisms, abnormal morphologies, abnormal protein folding patterns, and decreased functionality. In some cases, these mutations are somatic cell abnormalities only, and their resolution resolves the present disease condition. However, some mutations are germline mutations that, if not corrected, will be possibly inherited by future generations.

In the case of viral infections, many attempts have been made at producing vaccines, with limited success. In the case of HPV, HSV, SV, HIV, Coronavirus, and viral Hepatitis, few agents are effective at halting the progression of an active infection and none are known to succeed at destroying the virus in the cell.

In the case of bacterial infections, the growing phenomenon of drug-resistant microbes is presenting new challenges to those battling bacterial infections. For example, the growing proportion of patients with drug-resistant hospital-acquired infections, and the growing number of people exhibiting TB infections that are either multiple drug-resistant (MDR) or extensively drug-resistant (XDR) present a challenge of near-crisis proportions.

Hence, there is a need for a therapeutic agent that can be easily administered and is effective in the treatment of viral and bacterial infections and in possibly preventing and treating genetic disorders.

A list of the genes that are subject to regulation includes APC, ATM, BAP1, BARD1, BMPR1A, BRCA1, BRCA2, BRIP1, CDH1, CDK4, CDKN2A, CHEK2, DICER1, EPCAM, FH, GREM1, HOXB13, MITF, MLH1, MSH2, MSH6, MTHFR, MUTYH, NBN, NF1, PALB2, PMS2, POLD1, POLE, PPM1D, PTCH1, PTEN, RAD51C, RAD51D, SMAD4, STK11, and TP53. Table 1 describes the function of the above genes and the health condition(s) that result from mutations or other dysregulation.

TABLE 1

Genes and their functions

| Gene | Gene function and conditions arising from mutations. |
|---|---|
| APC<br>WNT signaling<br>pathway<br>regulator | The APC gene provides instructions for making the APC protein, which plays a critical role in several cellular processes. The APC protein acts as a tumor suppressor, which means that it keeps cells from growing and dividing too fast or in an uncontrolled way. It helps control how often a cell divides, how it attaches to other cells within a tissue, and whether a cell moves within or away from a tissue. This protein also helps ensure that the number of chromosomes in a cell is correct following cell division. The APC protein accomplishes these tasks mainly through association with other proteins, especially those that are involved in cell attachment and signaling.<br>One protein with which APC associates is beta-catenin. Beta-catenin helps control the activity (expression) of particular genes and promotes the growth and division (proliferation) of cells and the process by which cells mature to carry out specific functions (differentiation). Beta-catenin also helps cells attach to one another and is important for tissue formation. Association of APC with beta-catenin signals for beta-catenin to be broken down when it is no longer needed.<br>Mutations associated with cancers: Turcot Syndrome, gastric cancers, primary macronodular adrenal hyperplasia.<br>Mutations associated with other conditions: desmoid tumors associated familial adenomatous polyposis (FAP). Most people with FAP will develop colorectal cancer. |
| ATM:<br>serine/threonine<br>kinase | The ATM gene provides instructions for making a protein that is located primarily in the nucleus of cells, where it helps control the rate at which cells grow and divide. This protein also plays an important role in the normal development and activity of several body systems, including the nervous system and the immune system. Additionally, the ATM protein assists cells in recognizing damaged or broken DNA strands. DNA can be damaged by agents such as toxic chemicals or radiation. Breaks in DNA strands also occur naturally when chromosomes exchange genetic material during cell division. The ATM protein coordinates DNA repair by activating enzymes that fix the broken strands. Efficient repair of damaged DNA strands helps maintain the stability of the cell's genetic information.<br>Because of its central role in cell division and DNA repair, the ATM protein is of great interest in cancer research. |

TABLE 1-continued

Genes and their functions

| Gene | Gene function and conditions arising from mutations. |
|---|---|
| | ATM mutations can allow cells to die inappropriately, particularly affecting cells in a part of the brain involved in coordinating movements (the cerebellum). This loss of brain cells causes the movement problems characteristic of ataxia-telangiectasia.<br>Mutations associated with cancers: bladder, breast, melanoma, stomach, pancreas, lung, ovaries. |
| BAP1<br>BRCA1<br>associated<br>protein 1 | Although the exact mechanism is unclear, the BAP1 protein acts as a tumor suppressor. Tumor suppressor proteins help prevent cells from growing and dividing too rapidly or in an uncontrolled way. Although it is unclear exactly how changes in BAP1 function lead to BAP1 tumor predisposition syndrome, researchers speculate that altered activity of proteins normally regulated by BAP1 deubiquitination may promote cell proliferation or survival, resulting in tumor formation.<br>Mutations associated with cancers: cholangiocarcinoma, melanoma, uveal melanoma. |
| BARD1<br>BRCA1<br>associated<br>RING domain 1 | The BRCA1-BARD1 heterodimer specifically mediates the formation of 'Lys-6'-linked polyubiquitin chains and coordinates a diverse range of cellular pathways such as DNA damage repair, ubiquitination and transcriptional regulation to maintain genomic stability. Plays a central role in the control of the cell cycle in response to DNA damage. Acts by mediating ubiquitin E3 ligase activity that is required for its tumor suppressor function. Also forms a heterodimer with CSTF1/CSTF-50 to modulate mRNA processing and RNAP II stability by inhibiting pre-mRNA 3' cleavage.<br>Mutations associated with cancers: neuroblastoma, ovarian, breast. |
| BMPR1A:<br>bone<br>morphogenetic<br>protein receptor<br>type 1A | The bone morphogenetic protein receptor type 1A has a specific site into which certain other proteins, called ligands, fit like keys into locks. Specifically, the BMPR1A protein attaches (binds) to ligands in the transforming growth factor beta (TGF-β) pathway. This signaling pathway allows the environment outside the cell to affect how the cell produces other proteins. The BMPR1A receptor protein and its ligands are involved in transmitting chemical signals from the cell membrane to the nucleus.<br>Mutations associated with other conditions: Juvenile polyposis syndrome |
| BRCA1:<br>Breast cancer 1<br>DNA repair<br>associated | The BRCA1 gene provides instructions for making a protein that acts as a tumor suppressor. Tumor suppressor proteins help prevent cells from growing and dividing too rapidly or in an uncontrolled way.<br>The BRCA1 protein is involved in repairing damaged DNA. In the nucleus of many types of normal cells, the BRCA1 protein interacts with several other proteins to mend breaks in DNA.<br>Mutations associated with cancers: breast, ovarian, prostate, pancreatic, colon. |
| BRCA2:<br>Breast cancer 2<br>DNA repair<br>associated | The BRCA2 gene provides instructions for making a protein that acts as a tumor suppressor. Tumor suppressor proteins help prevent cells from growing and dividing too rapidly or in an uncontrolled way.<br>The BRCA2 protein is involved in repairing damaged DNA. In the nucleus of many types of normal cells, the BRCA2 protein interacts with several other proteins to mend breaks in DNA.<br>Mutations associated with cancers: Breast, ovarian, prostate, pancreatic, melanoma<br>Mutations associated with other conditions: Fanconi anemia |
| BRIP1:<br>BRCA1<br>interacting<br>protein C-<br>terminal<br>helicase 1 | DNA-dependent ATPase and 5' to 3' DNA helicase required for the maintenance of chromosomal stability. Acts late in the Fanconi anemia pathway, after FANCD2 ubiquitination. Involved in the repair of DNA double-strand breaks by homologous recombination in a manner that depends on its association with BRCA1.<br>Mutations associated with cancers: ovarian, breast<br>Mutations associated with other conditions: Fanconi anemia |
| CDH1:<br>cadherin 1 | The CDH1 gene provides instructions for making a protein called epithelial cadherin or E-cadherin. This protein is found within the membrane that surrounds epithelial cells, which are the cells that line the surfaces and cavities of the body, such as the inside of the eyelids and mouth. E-cadherin belongs to a family of proteins called cadherins whose function is to help neighboring cells stick to one another (cell adhesion) to form organized tissues.<br>Mutations associated with cancers: breast, hereditary gastric diffuse cancer, ovarian, prostate, endometrial.<br>Mutations associated with other conditions: Blepharocheilodontic (BCD) Syndrome, cleft lip & palate |
| CDK4:<br>cyclin<br>dependent<br>kinase 4 | Mutations in this gene as well as in its related proteins including D-type cyclins, p16(INK4a) and Rb were all found to be associated with tumorigenesis of a variety of cancers.<br>Mutations associated with cancers: melanoma, cutaneous malignant melanoma, |
| CDKN2A:<br>cyclin<br>dependent<br>kinase inhibitor<br>2A | The CDKN2A gene provides instructions for making several proteins. The most well-studied are the p16(INK4A) and the p14(ARF) proteins. Both function as tumor suppressors, which means they keep cells from growing and dividing too rapidly or in an uncontrolled way. Both proteins are also involved in stopping cell division in older cells (senescence).<br>Mutations associated with cancers: bladder, head & neck squamous cell, lung, melanoma |

TABLE 1-continued

Genes and their functions

| Gene | Gene function and conditions arising from mutations. |
|---|---|
| CHEK2: checkpoint kinase 2 | The protein encoded by this gene is a cell cycle checkpoint regulator and putative tumor suppressor. It contains a forkhead-associated protein interaction domain essential for activation in response to DNA damage and is rapidly phosphorylated in response to replication blocks and DNA damage. When activated, the encoded protein is known to inhibit CDC25C phosphatase, preventing entry into mitosis, and has been shown to stabilize the tumor suppressor protein p53, leading to cell cycle arrest in Gl. In addition, this protein interacts with and phosphorylates BRCA1, allowing BRCA1 to restore survival after DNA damage.<br>Mutations associated with cancers: Li-fraumeni Syndrome, ovarian, prostate, breast |
| DICER1: ribonuclease III | The DICER1 gene provides instructions for making a protein that plays a role in regulating the activity (expression) of other genes. The Dicer protein aids in the production of a molecule called microRNA (miRNA). MicroRNAs are short lengths of RNA, a chemical cousin of DNA. Dicer cuts (cleaves) precursor RNA molecules to produce miRNA.<br>Mutations associated with cancers: lungs, kidneys, ovaries, thyroid. |
| EPCAM: epithelial cell adhesion molecule | The EPCAM gene provides instructions for making a protein known as epithelial cellular adhesion molecule (EpCAM). This protein is associated with epithelial cells, which are the cells that line the surfaces and cavities of the body. The EpCAM protein is found spanning the membrane that surrounds epithelial cells, where it helps cells stick to one another (cell adhesion). In addition, the protein in the cell membrane can be cut at a specific location, releasing a piece called the intracellular domain (EpICD), which helps relay signals from outside the cell to the nucleus of the cell. EpICD travels to the nucleus and joins with other proteins, forming a group (complex) that regulates the activity of several genes that are involved in many cell processes, including growth and division (proliferation), maturation (differentiation), and movement (migration), all of which are important processes for the proper development of cells and tissues.<br>Mutations associated with other conditions: Lynch Syndrome, congenital tufting enteropathy |
| FH: fumarate hydratase | The FH gene provides instructions for making an enzyme called fumarase (also known as fumarate hydratase). Fumarase participates in an important series of reactions known as the citric acid cycle or Krebs cycle, which allows cells to use oxygen and generate energy. Specifically, fumarase helps convert a molecule called fumarate to a molecule called malate.<br>Mutations associated with cancers: Hereditary leiomyomatosis & renal cell cancer, primary macronodular adrenal hyperplasia.<br>Mutations associated with other conditions: Fumarase deficiency, |
| GREM1: gremlin 1, DAN family BMP antagonist | As an antagonist of BMP, this gene may play a role in regulating organogenesis, body patterning, and tissue differentiation. In mouse, this protein has been shown to relay the sonic hedgehog (SHE) signal from the polarizing region to the apical ectodermal ridge during limb bud outgrowth.<br>Mutations associated with other conditions: Polyposis Syndrome |
| HOXB13: Homeobox B13 | The HOXB13 gene provides instructions for producing a protein that attaches (binds) to specific regions of DNA and regulates the activity of other genes. On the basis of this role, the protein produced from the HOXB13 gene is called a transcription factor. The HOXB13 protein is part of a large group of transcription factors called the homeobox protein family. The HOXB13 protein is thought to play a role in the development and maintenance of the skin. It also acts as a tumor suppressor, which means that it keeps cells from growing and dividing too fast or in an uncontrolled way.<br>Mutations associated with cancer: prostate |
| MITF: melanocyte inducing transcription factor | The MITE gene provides instructions for making a protein called melanocyte inducing transcription factor. This protein plays a role in the development, survival, and function of certain types of cells. To carry out this role, the protein attaches to specific areas of DNA and helps control the activity of particular genes. On the basis of this action, the protein is called a transcription factor.<br>Mutations associated with cancer: melanoma<br>Mutations associated with other conditions: Tietz Syndrome, Waardenberg Syndrome |
| MLH1: mutL homolog 1 | The MLH1 gene provides instructions for making a protein that plays an essential role in repairing DNA. This protein helps fix errors that are made when DNA is copied (DNA replication) in preparation for cell division. It is a mismatch repair gene<br>Mutations associated with cancer: ovarian syndrome, Lynch Syndrome, constitutional mismatch repair deficiency syndrome |
| MSH2: mutS homolog 2 | The MSH2 gene provides instructions for making a protein that plays an essential role in repairing DNA. This protein helps fix errors that are made when DNA is copied (DNA replication) in preparation for cell division.<br>Mutations associated with cancer: ovarian syndrome, Lynch Syndrome, constitutional mismatch repair deficiency syndrome |

TABLE 1-continued

Genes and their functions

| Gene | Gene function and conditions arising from mutations. |
|---|---|
| MSH6: mutS homolog 6 | The MSH6 gene provides instructions for making a protein that plays an essential role in repairing DNA. This protein helps fix errors that are made when DNA is copied (DNA replication) in preparation for cell division. Mutations associated with cancer: ovarian syndrome, Lynch Syndrome, constitutional mismatch repair deficiency syndrome. |
| MUTYH: mutY DNA glycosylase | The MUTYH gene provides instructions for making an enzyme called MYH glycosylase, which is involved in the repair of DNA. This enzyme corrects particular errors that are made when DNA is copied (DNA replication) in preparation for cell division. Mutations associated with other conditions: familial adenomatous polyposis |
| NBN: nibrin | The MRE11A/RAD50/NBN complex interacts with the protein produced from the ATM gene, which plays an essential role in recognizing broken strands of DNA and coordinating their repair. Mutations associated with cancer: breast, prostate, ovarian, melanoma, leukemia. |
| NF1: Neurofibromin 1 | The NF1 gene provides instructions for making a protein called neurofibromin. This protein is produced in many types of cells, including nerve cells and specialized cells called oligodendrocytes and Schwann cells that surround nerves. These specialized cells form myelin sheaths, which are the fatty coverings that insulate and protect certain nerve cells. Mutations associated with cancer: Lung, juvenile myelomonocytic leukemia Mutations associated with other conditions: neurofibromatosis type 1 |
| PALB2: Partner and localizer of BRCA2 | This gene encodes a protein that may function in tumor suppression. This protein binds to and colocalizes with the breast cancer 2 early onset protein (BRCA2) in nuclear foci and likely permits the stable intranuclear localization and accumulation and repair of BRCA2. Mutations associated with cancer: ovarian, breast, pancreatic Mutations associated with other conditions: Fanconi anemia |
| PMS2: PMS1 homolog 2, mismatch repair system component | The PMS2 gene provides instructions for making a protein that plays an essential role in repairing DNA. This protein helps fix errors that are made when DNA is copied (DNA replication) in preparation for cell division. The PMS2 protein joins with another protein called MLH1 (produced from the MLH1 gene) to form a two-protein complex called a dimer. This complex coordinates the activities of other proteins that repair errors made during DNA replication. Repairs are made by removing the section of DNA that contains errors and replacing it with a corrected DNA sequence. The PMS2 gene is a member of a set of genes known as the mismatch repair (MMR) genes. Mutations associated with cancer: Ovarian cancer, constitutional mismatch repair deficiency syndrome, Lynch Syndrome Mutations associated with other conditions: alopecia areata |
| POLD1: DNA polymerase delta 1, catalytic subunit | DNA polymerase delta 1, catalytic subunit This gene encodes the 125-kDa catalytic subunit of DNA polymerase delta. DNA polymerase delta possesses both polymerase and 3' to 5' exonuclease activity and plays a critical role in DNA replication and repair. Mutations associated with cancers: mandibular hypoplasia, lipodystrophy syndrome, Colorectal cancer 10 Mutations associated with other conditions: deafness, progeroid features |
| POLE: DNA polymerase epsilon, catalytic subunit | This gene encodes the catalytic subunit of DNA polymerase epsilon. The enzyme is involved in DNA repair and chromosomal DNA replication. Mutations associated with cancer: colorectal cancer 12, Mutations associated with other conditions: facial dysmorphism, immunodeficiency, livedo, short stature, intrauterine growth retardation, metaphyseal dysplasia, adrenal hypoplasia congenita, genital anomalies. |
| PPM1D: protein phosphatase, Mg2+/Mn2+ dependent 1D | The protein encoded by this gene is a member of the PP2C family of Ser/Thr protein phosphatases. PP2C family members are known to be negative regulators of cell stress response pathways. The expression of this gene is induced in a p53-dependent manner in response to various environmental stresses. While being induced by tumor suppressor protein TP53/p53, this phosphatase negatively regulates the activity of p38 MAP kinase, MAPK/p38, through which it reduces the phosphorylation of p53, and in turn suppresses p53-mediated transcription and apoptosis. This phosphatase thus mediates a feedback regulation of p38-p53 signaling that contributes to growth inhibition and the suppression of stress induced apoptosis. Mutations associated with cancer: Familial breast. Mutations associated with other conditions: Intellectual developmental disorder with gastrointestinal difficulties and high pain threshold |
| PTCH1: Patched 1 | Patched-1 and Sonic Hedgehog function in a pathway that is essential for early development. This pathway plays a role in cell growth, cell specialization, and determining the shape (patterning) of many different parts of the developing body. When Sonic Hedgehog is not present, patched-1 prevents cells from growing and dividing (proliferating). When Sonic Hedgehog is attached, patched-1 stops suppressing cell proliferation. Based on its role in preventing cells from proliferating in an uncontrolled way, PTCH1 is called a tumor suppressor gene. Mutations associated with cancer: basal cell carcinoma, skin, medulloblastoma, breast, colon, 9q22.3 microdeletion |

TABLE 1-continued

Genes and their functions

| Gene | Gene function and conditions arising from mutations. |
|---|---|
| | Mutations associated with other conditions: coloboma, nonsyndromic holoprosencephaly, Gorlin Syndrome |
| PTEN: phosphatase and tensin homolog | The PTEN gene provides instructions for making an enzyme that is associated with almost all tissues in the body. The enzyme acts as a tumor suppressor, which means that it helps regulate cell division by keeping cells from growing and dividing too rapidly or in an uncontrolled way. The PTEN enzyme modifies other proteins and fats (lipids) by removing phosphate groups, each of which consists of three oxygen atoms and one phosphorus atom. Enzymes with this function are called phosphatases.<br>Mutations associated with cancer: prostate, endometrial, glioblastomas, astrocytomas, melanoma, bladder, lung, breast, head and neck squamous cell<br>Mutations associated with other conditions: autism spectrum disorder, Cowden Syndrome, Bannayan-Riley-Ruvalcaba Syndrome. |
| RAD51C<br>RAD51<br>paralog C | Essential for the homologous recombination (HR) pathway of DNA repair.<br>Involved in the homologous recombination repair (HRR) pathway of double-stranded DNA breaks arising during DNA replication or induced by DNA-damaging agents. Part of the RAD21 paralog protein complexes BCDX2 and CX3 which act at different stages of the BRCA1-BRCA2-dependent HR pathway. Upon DNA damage, BCDX2 seems to act downstream of BRCA2 recruitment and upstream of RAD51 recruitment; CX3 seems to act downstream of RAD51 recruitment; both complexes bind predominantly to the intersection of the four duplex arms of the Holliday junction (HJ) and to junction of replication forks.<br>Mutations associated with cancer: Fanconi anemia, ovarian cancer, breast cancer |
| RAD51D:<br>RAD51<br>paralog D | Involved in the homologous recombination repair (HRR) pathway of double-stranded DNA breaks arising during DNA replication or induced by DNA-damaging agents. Bind to single-stranded DNA (ssDNA) and has DNA-dependent ATPase activity. Part of the Rad21 paralog protein complex BCDX2 which acts in the BRCA1-BRCA2-dependent HR pathway. Upon DNA damage, BCDX2 acts downstream of BRCA2 recruitment and upstream of RAD51 recruitment.<br>Mutations associated with cancer: ovarian, breast-ovarian ? familial 4 |
| SMAD4:<br>SMAD family<br>member 4 | The SMAD4 protein serves both as a transcription factor and as a tumor suppressor. Transcription factors help control the activity of particular genes, and tumor suppressors keep cells from growing and dividing too fast or in an uncontrolled way.<br>Mutations associated with cancer: cholangiocarcinoma<br>Mutations associated with other conditions: juvenile polyposis, and blood vessel abnormalities other than hereditary hemorrhagic telangiectasia, hereditary hemorrhagic telangiectasia, Myhre Syndrome |
| STK11:<br>serine/threonine<br>kinase 11 | The STKI I gene (also called LKBI) provides instructions for making an enzyme called serine/threonine kinase 11. This enzyme is a tumor suppressor, which means that it helps keep cells from growing and dividing too fast or in an uncontrolled way. This enzyme helps certain types of cells correctly orient themselves within tissues (polarization) and assists in determining the amount of energy a cell uses. This kinase also promotes a type of programmed cell death known as apoptosis. In addition to its role as a tumor suppressor, serine/threonine kinase 11 function appears to be required for normal development before birth.<br>Mutations associated with cancer: Lung, breast, ovarian, non-small cell lung carcinoma, cervix, colorectal, melanoma, pancreatic.<br>Mutations associated with other conditions: Peutz-Jeghers Syndrome. |
| TP53:<br>Tumor protein<br>p53 | The TP53 gene provides instructions for making a protein called tumor protein p53 (or p53). This protein acts as a tumor suppressor' which means that it regulates cell division by keeping cells from growing and dividing (proliferating) too fast or in an uncontrolled way.<br>The p53 protein is located in the nucleus of cells throughout the body, where it attaches (binds) directly to DNA. When the DNA in a cell becomes damaged by agents such as toxic chemicals, radiation, or ultraviolet (UV) rays from sunlight, this protein plays a critical role in determining whether the DNA will be repaired or the damaged cell will self-destruct (undergo apoptosis). If the DNA can be repaired, p53 activates other genes to fix the damage. If the DNA cannot be repaired, this protein prevents the cell from dividing and signals it to undergo apoptosis. By stopping cells with mutated or damaged DNA from dividing, p53 helps prevent the development of tumors.<br>Mutations associated with cancer: brain tumor, colorectal, liver, osteosarcoma, rhabdomyosarcoma, adrenocortical carcinoma, melanoma, lung, bladder, breast, kidney (Wilms tumor), Li-Fraumeni Syndrome, cholangiocarcinoma, head & neck squamous cell carcinoma. |

Example list of viruses includes Human Papillomavirus (HPV), Herpes Simplex Virus (HSV), Simian Virus (SV), Coronavirus including SARS-Coronavirus, MERS-Coronavirus and SARS-COV2 (COVID-19) Coronavirus, Human Immunodeficiency Virus (HIV), Hepatitis Types A, B and C (Hep A, Hep B, Hep C). Example list of bacteria include bacteria includes mycoplasma and tuberculosis (TB) (including MDR TB and XDR TB).

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a method for treating disorders arising from the genetic mutation.

It is another object of the present invention that the composition can be easily administered.

It is still another object of the present invention that the method can be used to treat bacterial infections.

It is yet another object of the present invention that the method can be used to treat viral infections.

In one aspect, disclosed is a method of treating diseases and disorders resulting from genetic mutation, bacteria, and viruses. The method includes a step of administering a composition. The composition includes a dry admixture of L-carnitine tartrate [CAS 36687-82-8], pyridoxal-5'-phosphate [CAS 54-47-7] and fumaric acid [CAS 110-17-8]. The composition is also referred to herein as D-Boramine In one aspect, the composition can be used to treat the disorders resulting from dysregulation/mutation of APC, ATM, BAP1, BARD1, BMPR1A, BRCA1, BRCA2, BRIP1, CDH1, CDK4, CDKN2A, CHEK2, DICER1, EPCAM, FH, GREM1, HOXB13, MITF, MLH1, MSH2, MSH6, MTHFR, MUTYH, NBN, NF1, PALB2, PMS2, POLD1, POLE, PPM1D, PTCH1, PTEN, RAD51C, RAD51D, SMAD4, STK11 and TP53 genes.

In one aspect, the composition can be used in the treatment of diseases resulting from infestation by Human Papillomavirus (HPV), Herpes Simplex Virus (HSV), Simian Virus (SV), Coronavirus including SARS-Coronavirus, MERS-Coronavirus and SARS-COV2 (COVID-19) Coronavirus, Human Immunodeficiency Virus (HIV), Hepatitis Types A, B and C (Hep A, Hep B, Hep C), mycoplasma and tuberculosis (TB) (including MDR TB and XDR TB).

In one aspect, the disclosed composition can be used in the treatment of cancers, Antiphospholipid Syndrome, disseminate intravascular coagulation (DIC), familial adenomatous polyposis, familial adenomatous polyposis, neurofibromatosis Type 1, alopecia areata, deafness, coloboma, Nonsyndromic holoprosencephaly, Gorlin Syndrome, autism spectrum disorder, Cowden Syndrome, Bannayan-Riley-Ruvalcaba Syndrome, hereditary hemorrhagic telangiectasia, Myhre Syndrome, juvenile and adult polyposis Syndrome, Tietz Syndrome, Waardenberg Syndrome, Fancomi anemia, Blepharocheilodontic (BCD) Syndrome, Lynch Syndrome, congenital tufting enteropathy, and fumarase deficiency.

In one aspect, the composition can be administered orally. However, other routes of administration are within the scope of the present invention.

These and other objects and advantages of the embodiments herein and the summary will become readily apparent from the following detailed description.

DETAILED DESCRIPTION

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a method for the treatment of disorders arising from genetic mutations. The composition includes a dry admixture of L-carnitine tartrate, pyridoxal-5'-phosphate, and fumaric acid. The disclosed composition may include L-carnitine tartrate in a range of about 34-90%, pyridoxal-5'-phosphate in a range of about 5-33%, and fumaric acid in a range of about 0.5-33%. The disclosed composition may act by entering somatic and germline cells and enabling the mitochondria to repair the defects and restore non-mutated homeostasis to the cell and its intracellular signaling.

Experiments were performed to evaluate the effectiveness of the composition in encoding for proteins and correcting genetic SNPs that drive essential biological processes, such as development and differentiation, and when dysregulated, the potential development of complex diseases. Next-generation sequencing (NGS)-based RNA sequencing (RNA-Seq) is a highly sensitive and accurate tool that delivers a high-resolution, base-by-base view of coding and non-coding RNA activity for measuring gene expression across the transcriptome. This method can help elucidate previously undetected changes occurring in disease states, in response to therapeutics, under different environmental conditions. 36,900 tests were performed on the genes listed in Table 2 to confirm adequate functionality after taking an average dose of 1,000 mg of D-Boramine having 25 mg of pyridoxal-5'-phosphate daily for up to one year. Outcomes studies revealed gene function to improve in all SNPs tested thus suggesting a strong possibility of decreasing the chance of disease expression or decreasing severity of the active disease. Outcomes studies revealed after 500 to 8000 mg of D-Bora mine having 25 mg of pyridoxal-5'-phosphate. All of the genes listed in Table 2 confirmed adequate functionality within 12 months to possibly aid in disease prevention or recovery. Table 2 shows the list of genes evaluated and the functionality of the genes before administering D-Boramine. After supplementing with D-Boramine for up to one year, improvement in functionality increased as much as 93 to 100 percent.

TABLE 2

List of genes and their functionality before administering D-Boramine

| Gene | Functionality (%) |
| --- | --- |
| APC | 111 |
| ATM | 63 |
| BAP1 | 48 |
| BARD1 | 57 |
| BMPR1A | 47 |
| BRCA1 | 56 |
| BRCA2 | 53 |
| BRIP1 | 33 |
| CDH1 | 57 |
| CDK4 | 34 |
| CDKN2A | 35 |
| CHECK2 | 34 |
| DICER1 | 11 |
| EPCAM | 66 |
| FH | 40 |
| GREM1 | 19 |
| HOXB13 | 8 |
| MITF | 20 |
| MLH1 | 50 |
| MSH2 | 51 |
| MSH6 | 40 |
| MUTYH | 11 |
| NBN | 19 |
| NF1 | 12 |
| PALB2 | 19 |
| PMS2 | 26 |
| POLD1 | 12 |
| POLE | 5 |
| PPM1D | 19 |
| PTCH1 | 4 |
| PTEN | 47 |
| RAD51C | 25 |
| RAD51D | 9 |
| SMAD4 | 33 |
| STK11 | 44 |
| TP53 | 52 |

The above experiment suggests that DNA on the SNPs tested with revealed decreased functionality were low in L-Carnitine tartrate, fumaric acid and pyridoxal-5'-phosphate. D-Boramine appears to be successful in improving functionality in SNPs listed and may correct these mutations over time. L-Carnitine tartrate with pyridoxal-5'-phosphate and fumaric acid improved gene functionality up to 100 percent with no overexpression noted. L-carnitine increases the proliferative responses of both murine and human lymphocyte following mitogenic stimulation and increase polymorphonuclear chemotaxis. L-Carnitine assists with fatty acid transport across the cell membrane and improves mitochondrial function Furthermore, L-carnitine, even at minimal concentrations, neutralizes the lipid induced immunosuppression.

Fumaric acid is an acid regulatory thus likely creating a healthier pH in the cell. Much like Vitamin D, fumaric acid is formed by the body, in the skin during exposure to sunlight. It is related to malic acid and is involved in the production of energy derived from food. Fumaric acid is an intermediate product of the citric acid cycle that is a source of intracellular energy in the form of adenosine triphosphate (ATP). It is generated by oxidation of adenylsuccinate by the enzyme succinate dehydrogenase and is then converted to maleate by the enzyme fumarase. At present, fumaric acid esters (FAE) are licensed for the treatment of psoriasis. Several lines of evidence have demonstrated immunomodulatory effects for FAE. Clinical studies in psoriasis showed a reduction of peripheral CD4+- and CD8+-T-lymphocytes due to the ability of FAE to induce apoptosis. In vitro studies with the ester dimethyl fumarate (DMF) described an inhibitory effect on nuclear factor kappa B (NF-κB)-dependent transcription of tumor necrosis factor-alpha (TNF-α) induced genes in human endothelial cells. Animal studies using a model of central nervous system demyelination, MOG-induced experimental autoimmune encephalomyelitis (EAE), revealed a reduction of microglia and macrophages in inflamed lesions. A clinical study in relapsing-remitting multiple sclerosis (RRMS) patients with a modified fumaric acid ester, BG-12, showed as "proof of principle" a significant reduction in the number of gadolinium enhancing lesions after 24 weeks of treatment as compared to placebo.

The disclosed method includes a step of administering the composition through one of the different routes of administration known in the art for administering medicine in humans. Preferably, the composition can be administered through an oral route. The composition can be formulated in oral or liquid forms for oral administration to humans. Examples of the liquid formulation can include suspensions, syrups, and like. Examples of solid dosage forms can include tablets and capsules. The formulation may also include other ingredients which are substantially neutral and used for formulating the desired dosage form. Such ingredients are generally referred to as excipients. The disclosed dosage forms can be prepared by any of the methods known in the art for formulating oral dosage forms without departing from the scope of the present invention. The dose of D-Boramine in humans can be determined by known methods in the art. It is known that the actual dose may depend on the age and weight of a patient. In one case, the nominal adult dose of D-Boramine may be in a range of about 500-1000 mg/day. Depending on the specific condition and clinical presentation, a patient's daily dosage regimen may be adjusted from this nominal dose. Coronavirus, for example, responds well to a dose of 3000 mg/day for several days. The response to the treatment in a patient can optionally be evaluated using a suitable PCT test, the functioning of such PCT test is known to a skilled person.

Clinically, D-Boramine has shown to be useful as a therapeutic agent in treating a variety of viral diseases, cancers, and other diseases and in the permanent correction of certain regulatory genetic mutations to somatic and germline cells including, but not limited to, mutations of the APC, ATM, BAP1, BARD1, BMPR1A, BRCA1, BRCA2, BRIP1, CDH1, CDK4, CDKN2A, CHEK2, DICER1, EPCAM, FH, GREM1, HOXB13, MITF, MLH1, MSH2, MSH6, MTHFR, MUTYH, NBN, NF1, PALB2, PMS2, POLD1, POLE, PPM1D, PTCH1, PTEN, RAD51C, RAD51D, SMAD4, STK11, and TP53 genes.

The disease of viral origin that can be treated by administering D-Boramine can include Human Papillomavirus (all strains), Herpes Simplex Virus (strains 1, 2, and 6), Simian Virus (strains 5 and 40), Hepatitis (Types A, B, and C), Human Immunodeficiency Virus, Influenza A (all strains) and B (all strains), and Coronavirus (all strains but specifically including SARS, MERS, SARS-COV2, OC43 beta, NL 63 alpha, 229E alpha, HK, and HKU1 beta). The disease of bacterial origin includes mycoplasma and tuberculosis, including MDR TB and XDR TB may also be treated by administering D-Boramine. Other disease condition that may respond to administration of D-Boramine may include carnitine deficiency disorders, Antiphospholipid Syndrome, disseminate intravascular coagulation (DIC), familial adenomatous polyposis, familial adenomatous polyposis, neurofibromatosis type 1, alopecia areata, deafness, coloboma, nonsyndromic holoprosencephaly, Gorlin Syndrome, autism spectrum disorder, Cowden Syndrome, Bannayan-Riley-Ruvalcaba Syndrome, hereditary hemorrhagic telangiectasia, Myhre Syndrome, juvenile and adult polyposis syndrome, Tietz Syndrome, Waardenberg Syndrome, Fancomi anemia, Blepharocheilodontic (BCD) Syndrome, Lynch Syndrome, congenital tufting enteropathy, and fumarase deficiency.

Gene mutations listed in Table 2 are generally related to disorders including Non-Hodgkin's lymphoma, B-cell lymphoma, prostate, pancreatic, melanoma, cholangiocarcinoma, basal cell carcinoma, brain, colorectal, liver, osteosarcoma, rhabdomyosarcoma, adrenocortical carcinoma, melanoma, lung, bladder, breast, kidney (Wilms tumor), Li-Fraumeni Syndrome, head & neck squamous cell carcinoma. Lung, breast, ovarian, non-small cell lung carcinoma, cervical, Fanconi anemia, endometrial, glioblastomas, astrocytomas, bladder, lung, breast, skin, medulloblastoma, breast, colon, 9q22.3 microdeletion, juvenile myelomonocytic leukemia, leukemia, ovarian syndrome, Lynch Syndrome, constitutional mismatch repair deficiency syndrome, thyroid, Hereditary leiomyomatosis & renal cell, primary macronodular adrenal hyperplasia, Turcot Syndrome, gastric cancers, primary macronodular adrenal hyperplasia, uveal melanoma and other cancers arising from mutations to genes and the related change of genetic cell signals. Such disorders may be treated using the disclosed method by administering D-Boramine orally till the functionally of the associated gene reaches about 93-100%.

In the case of viral or bacterial infections, PCR analysis determines the presence of microbial DNA or RNA in human cells. After administration of D-Boramine, PCR analysis confirms that the patient cells no longer contain microbial DNA or RNA. The method was evaluated in the treatment of corona viral infection in humans. It is to be noted that D-Boramine is not an anti-viral or anti-microbial medicine. It is a proven nutritional formulation that strengthens the body's immune system to make a more effective defense against viral infections. In the study eighty-six patients, all presenting with COVID-19 symptoms, were confirmed as positive for COVID-19 via PCR testing. Of these 86 patients, the same PCR test revealed that 22 also had MERS-coronavirus, 33 also had SARS-coronavirus, and 49 had coronavirus (other). All patients were treated with D-Boramine 1500 mg oral/day until symptoms were resolved, (on an average 2-5 days). Elderly persons with preexisting respiratory or immune system issues required a longer dosing interval. Sixty-two (62) of the 86 persons receiving D-Boramine were PCR tested post-treatment and were confirmed to be clear of all viruses present during their PCR pretest.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A method of increasing the defense of a body in fighting SARS-COV2 (COVID-19) viral infection, the method comprising the step of orally administering D-Boramine composition that consists essentially of:

L-carnitine tartrate, pyridoxal-5'-phosphate, and fumaric acid, wherein the composition is administered in a dose of about 500-3000 mg/day.

2. The method according to claim 1, wherein the ingredients of the composition are present in a range of about:

L-carnitine tartrate—34-90%, pyridoxal-5'-phosphate—5-33%, and fumaric acid 0.5-33%.

3. The method according to claim 1, wherein the composition is present in the form of solid dosage form selected from a group consisting of tablets and capsules.

4. The method according to claim 1, wherein the composition is present in the form of liquid dosage.

5. The method according to claim 1, wherein the method further comprises the step of:

upon administering the composition, determining presence of viral DNA in the body after predetermined duration; and administering the composition every day till the viral DNA is detected in the body.

6. The method according to claim 5, wherein the viral DNA is detected using polymerase chain reaction (PCR) test.

* * * * *